US010867708B2

(12) United States Patent
Cocks et al.

(10) Patent No.: US 10,867,708 B2
(45) Date of Patent: Dec. 15, 2020

(54) SOCIAL VIRTUAL DIALYSIS CLINIC

(71) Applicant: Fresenius Medical Care Holdings, Inc., Waltham, MA (US)

(72) Inventors: Elijah E. Cocks, Winchester, MA (US); Stacy Blasberg, Needham, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 687 days.

(21) Appl. No.: 15/040,138

(22) Filed: Feb. 10, 2016

(65) Prior Publication Data

US 2017/0011175 A1 Jan. 12, 2017

Related U.S. Application Data

(60) Provisional application No. 62/190,825, filed on Jul. 10, 2015.

(51) Int. Cl.
| | | |
|---|---|---|
| *G16H 80/00* | (2018.01) | |
| *G16H 10/60* | (2018.01) | |
| *G16H 40/20* | (2018.01) | |
| *H04L 29/06* | (2006.01) | |
| *H04L 29/08* | (2006.01) | |

(52) U.S. Cl.
CPC ............ *G16H 80/00* (2018.01); *G16H 10/60* (2018.01); *G16H 40/20* (2018.01); *H04L 65/403* (2013.01); *H04L 67/12* (2013.01)

(58) Field of Classification Search
CPC ..... G06F 19/3418; G16H 10/60; G16H 50/20
See application file for complete search history.

(56) References Cited

U.S. PATENT DOCUMENTS

| | | | |
|---|---|---|---|
| 6,559,863 B1* | 5/2003 | Megiddo | H04L 12/1827 348/14.08 |
| 8,265,957 B2 | 9/2012 | Craine | |
| 8,769,625 B2 | 7/2014 | Wang et al. | |
| 9,635,111 B2 | 4/2017 | Wang et al. | |
| 2008/0149551 A1* | 6/2008 | Brugger | A61M 1/3441 210/232 |
| 2008/0208912 A1* | 8/2008 | Garibaldi | G06Q 10/06 |

(Continued)

OTHER PUBLICATIONS

Marina U. Bers et al., "Zora: A Pilot Virtual Community in the Pediatric Dialysis Unit," MEDINFO 2001, pp. 800-804.

(Continued)

*Primary Examiner* — Jonathan Durant
(74) *Attorney, Agent, or Firm* — Fish & Richardson P.C.

(57) ABSTRACT

A social virtual dialysis clinic is provided that simulates social community aspects of a clinic group environment for patients undergoing a medical treatment away from a clinic. The described social virtual dialysis clinic system provides for integrated display devices for medical treatment information functionality, such as for dialysis treatment, with social interaction capabilities among multiple remotely-located patients while the patients are undergoing medical treatments at home or while traveling. Scheduling of the patients as participants in the social virtual dialysis clinic may be performed by a remote computer that receives transmitted information from each of the medical treatment machines performing medical treatments, respectively, on the patients.

20 Claims, 7 Drawing Sheets

(56) References Cited

U.S. PATENT DOCUMENTS

| | | |
|---|---|---|
| 2010/0137693 A1 | 6/2010 | Porras et al. |
| 2010/0269055 A1* | 10/2010 | Daikeler ............... A63B 24/00 |
| | | 715/757 |
| 2011/0125844 A1 | 5/2011 | Collier et al. |
| 2011/0265008 A1* | 10/2011 | Levine ............... G06F 19/3418 |
| | | 715/738 |
| 2012/0066140 A1 | 3/2012 | Hegeman et al. |
| 2013/0086507 A1* | 4/2013 | Poston ................. G06F 3/0483 |
| | | 715/777 |
| 2014/0012595 A1 | 1/2014 | Fox et al. |
| 2014/0074454 A1 | 3/2014 | Brown et al. |
| 2014/0121845 A1 | 5/2014 | Mueller |
| 2014/0164519 A1 | 6/2014 | Shah |
| 2014/0266983 A1 | 9/2014 | Christensen |

OTHER PUBLICATIONS

"DaVita Introduces Innovative Social Networking Tool for Dialysis Patients," Business Wire, Dec. 14, 2010, 2 pp.

Bers et al., "Identity construction environments: Supporting a Virtual Therapeutic Community of Pediatric Patients Undergoing Dialysis", Proceedings of the SIGCHI Conference on Human factors in Computing Systems, 3(1):380-387, ACM Mar. 2001.

International Preliminary Report on Patentability in International Application No. PCT/US2016/040379, dated Jan. 16, 2018, 9 pages.

International Search Report and Written Opinion in International Application No. PCT/US2016/040379, dated Oct. 24, 2016, 11 pages.

Palm, "A Declaration of Healthy Dependence: The Case of Home Care", Health Care Analysis, 22(4):385-404, Oct. 2012.

* cited by examiner

SOCIAL VIRTUAL DIALYSIS CLINIC

RELATED APPLICATION

This application claims priority to U.S. Provisional App. 62/190,825, filed Jul. 10, 2015, entitled "Social Virtual Dialysis Clinic," which is incorporated herein by reference.

TECHNICAL FIELD

This application relates to the field of virtualized environments and medical treatments.

BACKGROUND

Dialysis is a medical treatment used to support a patient with insufficient renal function. The two principal dialysis methods are hemodialysis and peritoneal dialysis.

During hemodialysis (HD), a patient's blood is passed through a dialyzer of a dialysis machine while also passing a dialysis solution or dialysate through the dialyzer. A permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood. An HD treatment typically lasts a few hours and may be performed multiple times a week on the patient.

During peritoneal dialysis (PD), a patient's peritoneal cavity is periodically infused with sterile aqueous solution, referred to as PD solution or dialysate. The membranous lining of the patient's peritoneum acts as a natural permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Hemodialysis treatments are typically performed on a patient multiple times a week using an HD machine in a clinic or home environment with each treatment lasting a least a few hours. Peritoneal dialysis treatments are done several times a day on a patient, often at home and often performed overnight while a patient is asleep using an automated PD machine or cycler. Dialysis machines are typically equipped with interfaces for receiving inputs and providing information to users during treatments.

Home dialysis gives the freedom to lead a more normal work and social life, and according to some research, may offer better health outcomes. Home dialysis machines exist that are configured for performing HD or PD treatments at home and/or otherwise remote from a clinic. However, even with the availability of home dialysis treatments, the in-center or clinic setting is popular with patients because of the community feeling and support structure provided by nurses, patient care technicians and other patients all experiencing the same environment.

Social media, a term given to widely-available Internet-based platforms that facilitate information sharing of user-generated content, such as social networking sites, media-sharing sites, blogs, microblogs and wikis, have transformed the way society communicates. Through community building, message amplification, rapid dissemination and on-line engagement, social media has changed societal interactions and relationships. Health care is one field that continues to experience advantageous ramifications from the proliferation of social media and other Internet-based communication platforms.

Accordingly, it would be desirable to provide a system that enables simulated in-center social aspects of community and support for a patient while that patient is receiving treatment at home or otherwise remote from a clinic.

SUMMARY

A social virtual dialysis clinic may simulate and facilitate social aspects of a clinic group environment for patients undergoing a medical treatment away from a clinic. The social virtual dialysis clinic system described herein provides for integrated medical treatment information functionality, such as a dialysis treatment, with social media/community capabilities for a simulated social in-clinic environment while patients are undergoing medical treatments at home or while traveling.

According to the system described herein, a device is provided for performing medical treatments and simulating social aspects of a medical clinic environment. The device includes a medical treatment machine configured to perform a medical treatment. A medical treatment information display displays medical treatment information of the medical treatment performed by the medical treatment machine. A social interaction information display displays social interaction information of multiple users. The medical treatment information display and the social interaction information display are integrated into an interactive display device that interfaces with a remote computer to exchange information with the remote computer. A characteristic of the medical treatment being performed by the medical treatment machine is transmitted to the remote computer and is used in scheduling multiple participants for remote social interaction using the interactive display device while the medical treatment machine performs the medical treatment. The scheduling may be performed automatically by the remote computer according to a commonality in the characteristic of the medical treatment among each of the multiple participants.

In various embodiments, the interactive display device wirelessly exchanges information with the remote computer, for example, either directly with the remote computer or via an intermediary device, and in which the intermediary device may be a transceiver device of the medical treatment machine. The interactive display device may be incorporated into the medical treatment machine or may be remote from the medical treatment machine. The interactive display device may be a portable processing device carried or worn by a user that displays information to the user and receives input from the user. The medical treatment machine may be a dialysis machine, and the characteristic of the medical treatment may include a treatment type, a treatment length, a frequency of treatment and/or a time of day of treatment.

According further to the system described herein, a social virtual dialysis clinic system includes a first medical treatment machine that is configured to perform a first medical treatment on a first user and a second medical treatment machine, remote from the first medical treatment machine, that is configured to perform a second medical treatment on a second user. A first medical treatment information display, coupled to the first medical treatment machine, displays medical treatment information of the first medical treatment machine. A first social interaction information display, coupled to the first medical treatment machine, displays social interaction information of the first user and the second user. The first medical treatment information display and the first social interaction information display are integrated into a first interactive display device that interfaces with a remote computer to exchange information with the remote computer. A second medical treatment information display, coupled to the second medical treatment machine, displays medical treatment information of the second medical treatment machine. A second social interaction information display, coupled to the second medical treatment machine, displays social interaction information of the first user and the second user, wherein the second medical treatment information display and the second social interaction information display are integrated into a second interactive display device that interfaces with the remote computer to exchange information with the remote computer.

In various embodiments, a first characteristic of the first medical treatment being performed by the first medical treatment machine is transmitted to the remote computer, and a second characteristic of the second medical treatment being performed by the second medical treatment machine is transmitted to the remote computer. The first characteristic and the second characteristic are used in scheduling participants for remote social interaction using the first interactive display device and the second interactive display device while the first and second medical treatment machines perform the first and second medical treatments. The first and/or the second interactive display devices wirelessly exchange information directly with the remote computer and/or wirelessly exchange information with the remote computer via an intermediary device that may be a transceiver device of at least one of the medical treatment machines. At least one of the first and the second interactive display devices may be incorporated into a corresponding one of the first or the second medical treatment machines and/or may be remote from a corresponding one of at least one of the first and the second medical treatment machines. At least one of the first or the second interactive display devices may be a portable processing device carried or worn by a user that displays information to the user and receives input from the user. At least one of the first or the second medical treatment machines may be a dialysis machine and the first characteristic and/or the second characteristic may include a treatment type, a treatment length, a frequency of treatment and/or a time of day of treatment.

BRIEF DESCRIPTION OF THE DRAWINGS

Embodiments of the system described herein are explained with reference to the several figures of the drawings, which are briefly described as follows.

DETAILED DESCRIPTION OF VARIOUS EMBODIMENTS

According to the system described herein, technologies behind existing social media platforms, sites or gaming forums, along with still photos, web cameras and/or microphones/speakers, may be used to facilitate remote interaction among home dialysis users or patients to give them a simulated or "virtual" clinic feel during home treatments. Each home user or patient may choose to join a virtual clinic group of other users similarly undergoing dialysis treatment at home, away from a clinic and/or with clinic patients who are participating in the virtual dialysis clinic environment. No matter the time of day or day of the week, users may employ a world-wide network to identify folks undergoing treatment. Groups may be private (e.g. registration/subscription based groups) or public (e.g. public chat rooms/message boards). Patients may be identified or anonymous. User names, profiles and/or any sensitive medical information used in scheduling according to the system described herein may be controlled in accordance with appropriate law, policies and procedures (e.g. HIPPA) for protecting medical and/or other sensitive information. Users may create their own recurring groups of the same people, or "smart" software can be used to identify people to group together based on time of day or frequency of dialysis treatments. Information used to form the groups may be obtained from a remote and/or central server that receives and stores information from at-home treatments.

In an embodiment of the system described herein, a device is provided that integrates dialysis treatment information display and social media display functionality in real-time and utilizing a captive audience of a known group of patients. The displays of the treatment information and social media functionality may be integrated onto a display of the dialysis machine. The dialysis machine may communicate with a remote and/or central server via a network to access and/or provide information of patients undergoing at-home treatments. Alternatively, the displays of information may be integrated and displayed on a portable processing device, such as a tablet, smartphone and/or other processing unit of the patient. In various embodiments, the portable processing device may be communicatively coupled to the dialysis machine via a short range communication technology, such as Bluetooth, a WiFi based communication technology, and/or a near field communication (NFC) technology.

Figure 1:
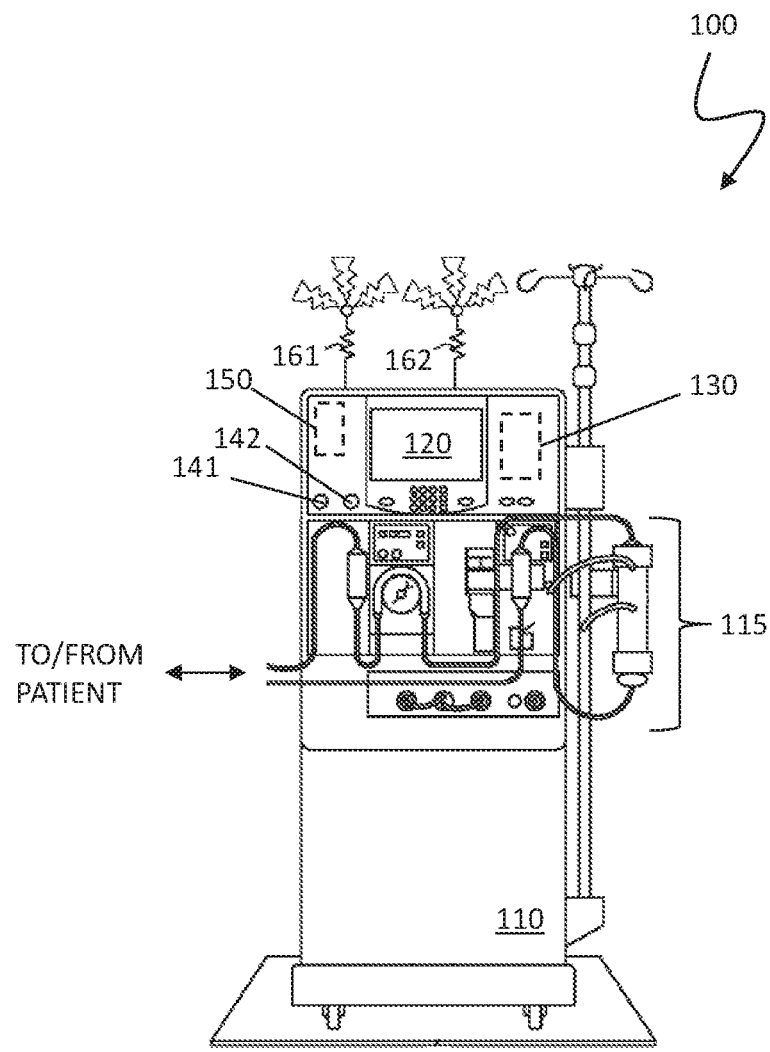
FIG. 1 is a schematic illustration showing an example of a dialysis system having social virtual dialysis clinic features in accordance with an embodiment of the system described herein.

FIG. 1 shows a dialysis system having social dialysis clinic features and functionality in accordance with an embodiment of the system described herein. The dialysis system 100 includes a dialysis machine 110 with one or more dialysis components 115 for performing a dialysis treatment. In an embodiment, the dialysis system 100 may be a hemodialysis system and the dialysis machine 110 may be a hemodialysis machine. The hemodialysis system may be a home or portable hemodialysis system for performing hemodialysis at home and/or otherwise remote from a clinic. The dialysis machine 110 includes a display 120 that may be a touchscreen display and/or may have other display control or interface components, including non-contact interfacing components. Although a hemodialysis system, particularly a portable or home hemodialysis system, is principally discussed herein, it is noted that the system described herein may be used in connection with other types of dialysis systems, including peritoneal dialysis systems, and/or other types of medical devices or machines performing a medical treatment (e.g. chemotherapy) at home and/or otherwise remote from a clinic.

The dialysis machine 110 includes a control unit 130 (e.g. a processor) and one or more interface components 141, 142. The interface components 141, 142 may include user interface components that may enable a user to activate and/or otherwise engage with the social interaction functionality of the social virtual dialysis clinic, as discussed in further detail elsewhere herein. The interface components 141, 142 may be configured such that the user engages with the social interaction capabilities of the system described herein using the components 141, 142 during performance of a medical treatment by the dialysis machine 110. In an embodiment, the interface components 141, 142 may include a camera unit 141 that provides for real time image/video interaction of the user with other users in the social virtual dialysis clinic and a microphone/speaker 142 that enables real time audio interaction of the user with other users in the social virtual dialysis clinic. Information of the social interaction may be displayed on the display 120 in a manner that does not interfere with display of information concerning the dialysis treatment being performed by the dialysis machine 110. Other interaction devices and/or sensors may be used in connection with the interface components 141, 142. The control unit 140 can receive signals from, and transmit signals to, the display 120, the interface components 141, 142, and/or other components of the dialysis system 100.

The dialysis machine 110 may also include a data storage and/or transmission component 150 that may be coupled to the control unit 140 and that may enable the storage of data on the dialysis machine and/or the transmission of data to and from the dialysis machine 110 in connection with the social virtual dialysis clinic features discussed herein. The data storage and/or transmission component may be coupled to one more wireless antennas 161, 162 and/or other wireless signal devices that enable receiving and transmitting wireless signals. In some embodiments, the one or more wireless antennas 161, 162 may represent antennas for different modalities of wireless communication, for example, an antenna 161 for short range wireless communications and an antenna 162 for telecommunication network communications, among other possibilities. In other embodiments, the wireless communication modalities of the system described herein may be performed using only one antenna. In various implementations, the data may include prescription information, treatment data and/or other therapy-based data and/or may include authorization information and/or other user profile-based information.

The components for wireless data transmission, such as components 150, 161, 162, may include components for short range wireless transmission technologies, such as Bluetooth or NFC technologies, components for communication with one or more peripheral devices including use of a WiFi network, and/or network transmission components for transmitting and receiving data or other signals wirelessly via a telecommunications network and/or the Internet using one or more computers. In connection with storage or transmission, data may be secured and/or encrypted via the control unit 130 using appropriate security and encryption protocols according to applicable laws and regulations governing storage or transmission of sensitive data and/or protected medical information. In particular, the data user in the scheduling and coordination of the users of the virtual dialysis clinic environment may be appropriately safeguarded in connection with appropriate standards.

Figure 2:
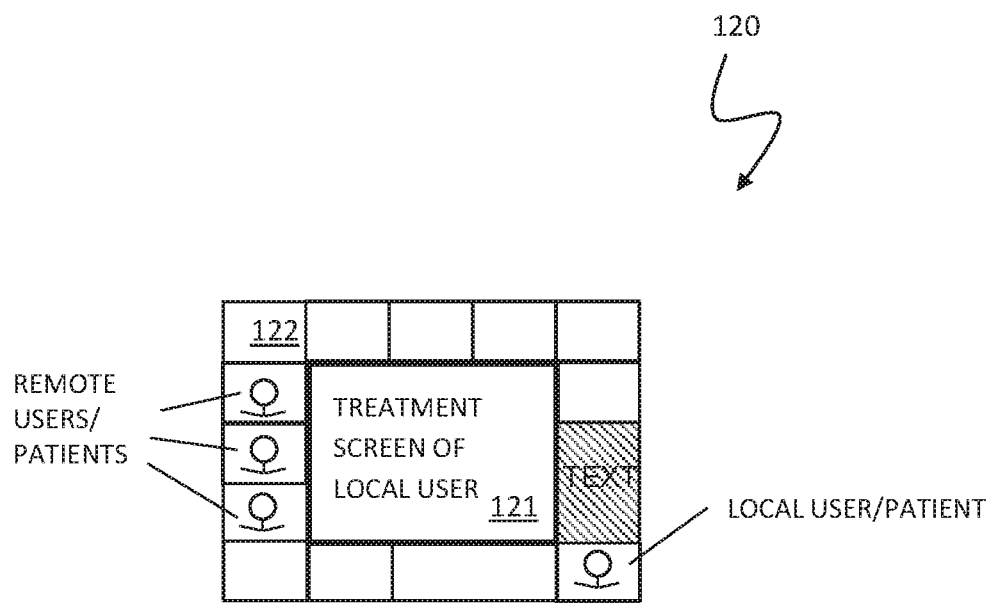
FIG. 2 is a schematic illustration showing an integrated display of social media/community interaction functionality with medical treatment information on a device accessible to a user according to an embodiment of the system described herein

FIG. 2 is a schematic illustration showing an integrated information display of social interaction information/functionality with medical treatment information on a display accessible to a user. In an embodiment, as illustrated, the integrated information displays for dialysis treatment information 121 and social interaction information 122 may be presented on the display 120 of the dialysis machine 110 that is described elsewhere herein. In the illustrated example, the dialysis treatment information 121 is presented in the middle of the display 120 and the social interaction information 122, that may include images (e.g. still photos or video) representing the local user (e.g. a patient) and remote users (e.g. other patients) as well as text based interaction capabilities, is shown around the periphery of the display 120. Other information layouts may be used as desirable and appropriate in specific contexts. In an embodiment, the layout of the dialysis treatment information and the social interaction information enables the local user to participate in the social interaction with other remote users in a manner that also facilitates appropriate visual monitoring of the dialysis treatment information by the local user undergoing the dialysis treatment due to the proximal positioning of the dialysis treatment information and the social interaction information on the single display 120.

In this embodiment, the social media functionality and components thereof are integrated with the dialysis machine, enabling one device to perform the medical treatment and facilitate the social interactions of the virtual clinic environment between a local user of the dialysis machine and other users/patients located remotely from the local user. It is noted that the users are primarily described as patients, but may also include medical personnel, such as doctor, nurses and/or other patient care technicians. In an aspect, integration of the social interaction information display and the medical treatment information display onto a single interactive display may advantageously enable the local patient to participate in the social interaction with other remote patients in a manner that also facilitates appropriate visual monitoring of medical treatment information by the local patient undergoing the medical treatment due to the proximal positioning of the medical treatment information and the social interaction information on the single display.

Additionally and/or alternatively, in another embodiment, the information displays of the social interaction information and medical treatment information may be integrated and displayed on a portable processing device, such as a tablet, smartphone and/or other processing unit of the patient. In various embodiments, the portable processing device may be coupled to the dialysis machine via a short range communication technology, such as Bluetooth and/or NFC technology. The local user may hold the portable processing device and participate in the virtual clinic environment provided by the social interaction functionality on the remote display while still being kept of apprised of the dialysis treatment information that may also be shown on the remote display held by the local user. As further discussed elsewhere herein, the layout of the medical treatment information and the social interaction information on the interactive display of the portable processing unit may enable the local user to participate in the social interaction with other remote users in a manner that also facilitates appropriate visual monitoring of the medical treatment information by the local user undergoing the medical treatment due to the proximal positioning of the medical treatment information and the social interaction information on the interactive display.

In various implementations, the medical treatment information displayed may be information corresponding to that of a dialysis treatment being performed on a patient and include information suitable for display to a patient in a home dialysis setting. Other information of the dialysis treatment may be stored and transmitted to and/or accessible by a clinician or other health care practitioner according to appropriate transmission mechanisms and protocols, including wireless transmission of data to a remote computer. For further discussion of example implementations for remote control of, and data display on or transmission to/from, a dialysis machine, reference is made to U.S. Pat. No. 8,769,625 B2 to Wang et al., entitled "Remote Control of Dialysis Machines," which is incorporated herein by reference. The social interaction information displayed may include information exchange enabled by social media based platforms, including text, pictures, audio and/or video exchanges, as further discussed elsewhere herein, and that may be facilitated using a remote server or computer that schedules and hosts one or more instances of the social virtual dialysis clinic among participants.

Figure 3:
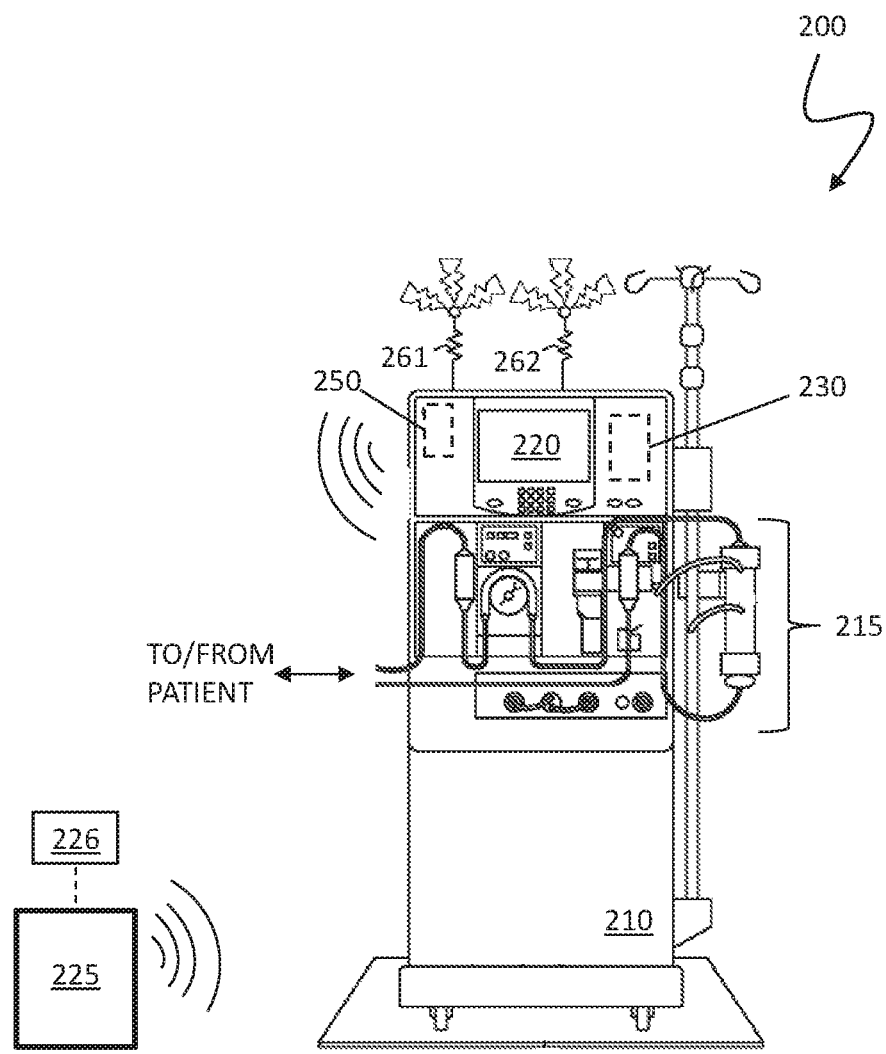
FIG. 3 is a schematic illustration showing a dialysis system having a display remote from dialysis machine, in which the remote display is being held or operated by a user according to an embodiment of the system described herein.

FIG. 3 is a schematic illustration showing a dialysis system 200 having a remote display 225 remote from dialysis machine 210, in which the remote display 225 is being held or operated by a user. The remote display 225 may be a hand-held computing device, such as a smartphone, tablet or other portable processing and display device. In other embodiments, as further discussed elsewhere herein, the remote display 225 may be a wearable device that is worn and operated by the user. The remote display 225 provides an integrated information display of social interaction information/functionality in connection with performance of a medical treatment. The remote display 225 may include integrated interfacing components such as a microphone and/or a camera that may enable a user to engage in real-time with the social interaction functionality of the virtual dialysis clinic according to the system described herein. Alternatively, one or more other separate interfacing components 226, e.g. a separate microphone/speaker and/or camera unit, may be included that may have a wired and/or wireless connection to the remote display 225 to enable the real-time engagement with the social interaction functionality of the system. The remote display 225 may be in communicative contact with the dialysis machine 210 via a wired and/or wireless connection. In the illustration, a wireless connection between the remote display 225 and the dialysis machine 210 is shown and, in an embodiment, the wireless connection may be a short range wireless connection, e.g., Bluetooth and/or NFC. In the figure, components of the dialysis system 200 that are similar to the components shown and described in connection with the dialysis system 100 correspond to that of the dialysis system 100 but are instead prefaced with the numeral "2".

Figure 4:
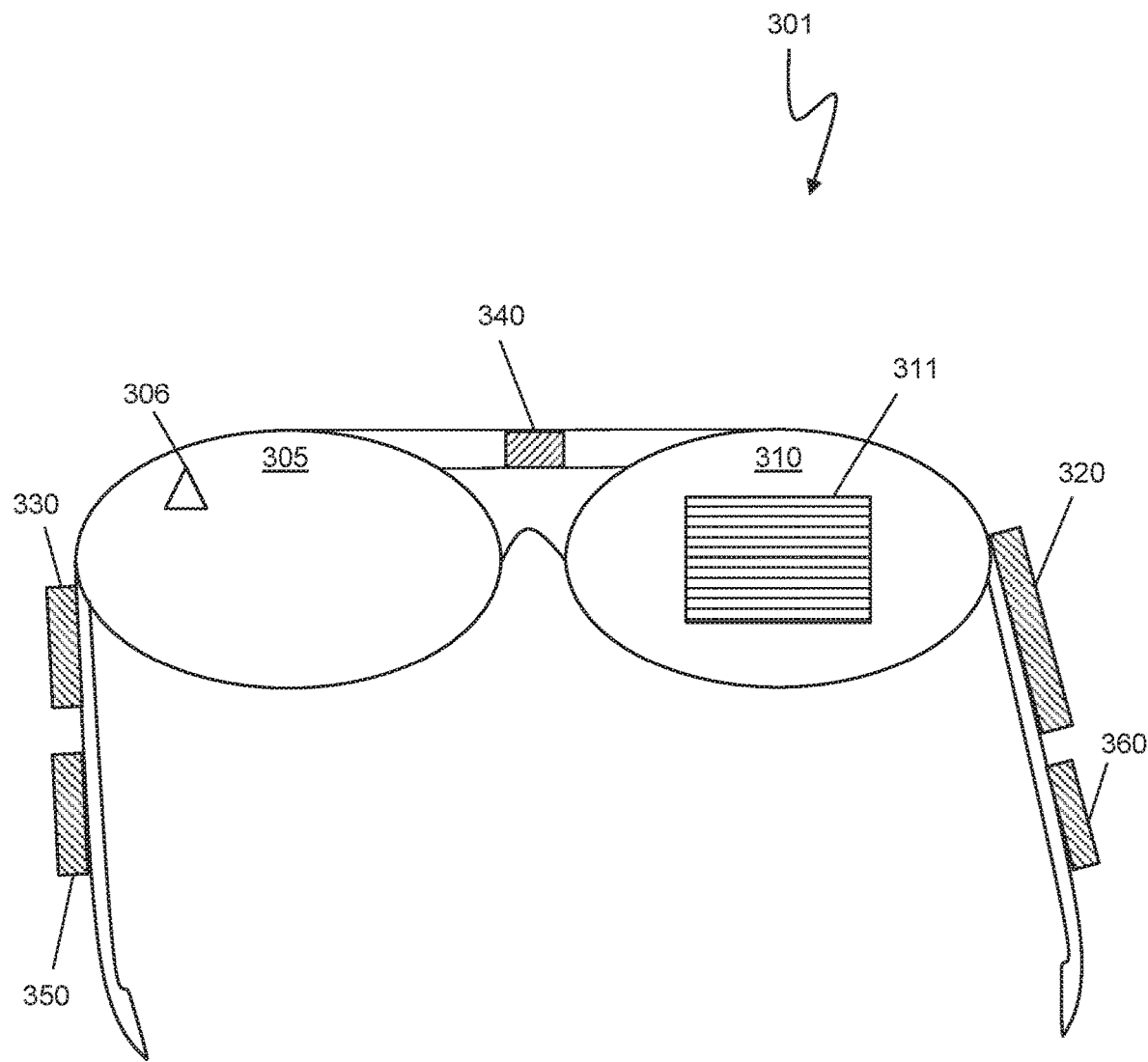
FIG. 4 is a schematic illustration of a wearable interface device that may be used in accordance with an embodiment of the system described herein.

FIG. 4 is a schematic illustration of a wearable interface device 301 that may be used in accordance with an embodiment of the system described herein. The wearable interface device 301 may be an implementation of the remote display 225 described in connection with FIG. 3. As discussed elsewhere herein, the remote display 225 may also include handheld devices, such as tablets and/or smartphones among other types of portable computing devices. The wearable interface device 301 may be worn by the user in connection with remotely monitoring a dialysis machine or component during a dialysis treatment and in connection with engaging in the social interaction functionality of the virtual dialysis clinic, as further discussed in detail elsewhere herein. The wearable interface device 301 is principally shown and described herein in connection with an implementation as a head-mounted device, such as smartglasses. However, other wearable display implementation may be used in connection with the system described herein, including other types of head-mounted displays and/or other types of wearable computing devices, such as a wrist watch-style implementation, e.g. a smartwatch.

The wearable interface device 301 may include two sides with screens 305, 310 that may be used and function independently of each other. For example, in an embodiment, the screen 305 may be clear to enable a user to perform duties remote from the dialysis machine and unobstructed by any visual display during use of the wearable interface device 301, and the screen 310 may display information 311 used in connection with monitoring and/or controlling the dialysis machine 210 or component thereof. Alternatively, for example, the screen 305 may include a symbol 306 that indicates an alert and is presented in a manner that does not obstruct a view through the wearable interface device 301. In other embodiments, different types of information sent to, or generated by, the wearable interface device 301 may be displayed on either of the screens 305, 310 and, when not in use, both of the sides may be transparent, for example.

In an embodiment, the wearable interface device 301 may be communicatively paired with the dialysis machine 210. The wearable interface device 301 may receive certain information wirelessly transmitted from the dialysis machine 210 in connection with pairing or authenticating the wearable interface device 301 with the dialysis machine 210 and/or in connection with acknowledging signals sent by the wearable interface device 301 to the dialysis machine 210. In an embodiment, the symbol 306 on the screen 305 may indicate a successful pairing of the wearable interface device 301 with the dialysis machine 210.

In an embodiment, the information 311 may be a screen similar to that being displayed on the display 220 of the dialysis machine 210 and/or may present other information in connection with the dialysis treatment and/or other functions performed by the dialysis machine 210, as further discussed in detail elsewhere herein. In various other embodiments, the information 311 displayed on the wearable interface device 301 may include an alert when an alarm of the dialysis machine 210 is triggered. Other types of information may also be displayed.

In an embodiment, in connection with the information 311 displayed on the wearable interface device 301, the wearable interface device 301 may receive information wirelessly transmitted by the dialysis machine 210. The wearable interface device 301 may include a transceiver device 320 that receives and/or transmits signals according to the functionality discussed herein. The transceiver device 320 may include one or more processors to process the signals in connection with the display of the information 311 and in connection with the transmission of information concerning the dialysis treatment being performed by the dialysis machine 210. The transceiver device 320 may further include a memory, and/or other non-transitory computer-readable medium, to store data in connection with the information transmitted and/or received by the wearable interface device 301 and in connection with the execution of software or other executable code in connection with the operations of the wearable interface device 301 both in connection with the dialysis treatment being performed and the social interaction functionality of the virtual dialysis clinic.

For example, the wearable interface device 301 may include a command recognition device 330 that recognizes and interprets commands in connection with operation of the wearable interface device 301, specifically in connection with selection, control and activation of elements on the screens 305, 310 of the wearable interface device 301. In various embodiments, the commands may be gestures recognized and used by a gesture-recognition module of the command recognition device 330 in connection with the operation of the wearable interface device 301. The gestures may include, for example, hand gestures, head gestures and/or eye gestures of the user. In other embodiments, the command recognition device 330 may include a voice recognition module that enables voice-based operation of the wearable interface device 301. The command recognition capability enables hands-free, non-contact operation of the wearable interface device and remote monitoring of the dialysis machine according to the system described herein.

The wearable interface device 301 may further include a camera 340 that may be used in connection with capturing images that may be displayed and/or used by the interface device 301, as further discussed in detail elsewhere herein. In various embodiments, the camera 340 may also include video capabilities. It is noted that although the devices 320, 330 and 340 are shown as separate devices, in other embodiments, the functionalities of these devices may be incorporate into one integral device disposed on the interface device 301. It is also noted that the devices 320, 330 and/or 340 may be detachable and communicationally coupled (e.g. wirelessly) and/or otherwise portable or manipulable to enable the user to position the devices in a desired location for appropriate functionality. Further, the interface device 301 may include a power source 350, such as a battery.

The wearable interface device 301 may further include an audio input/output device 360 that may include a speaker and/or a microphone. The audio device 360 may enable the user to hear and provide audible signals such that an intercom-type verbal exchange may be enabled between the user wearing the interface device 301 and other users/patients of the virtual dialysis clinic. In various embodiments, the audio device 360 may also operate in connection with voice command recognition capability of the command recognition device 330, as further discussed elsewhere herein. It is also noted that the processing of the wearable interface device 301 may enable the interface device to recognize a verbal communication from the patient that is then converted into text and displayed on one or more of the screens 305, 310. In connection therewith, the processing of the interface device 301 may enable translation capabilities. For example, a patient may make a verbal communication at the dialysis system 200 (and/or other remote dialysis system) in one language (such as Spanish) and the verbal communication is converted into text and then translated into another language (such as English) via processing capabilities of the wearable interface device 301 and the translated text displayed on one or more of the screens 305, 310 of the wearable interface device 301.

For further discussion and examples of a wearable interface device having aspects that may be used in connection with the system described herein, reference is made to US 2014/0266983 A1 to Christensen, entitled "Wearable Interface for Remote Monitoring and Control of a Medical Device," which is incorporated herein by reference.

Figure 5A:
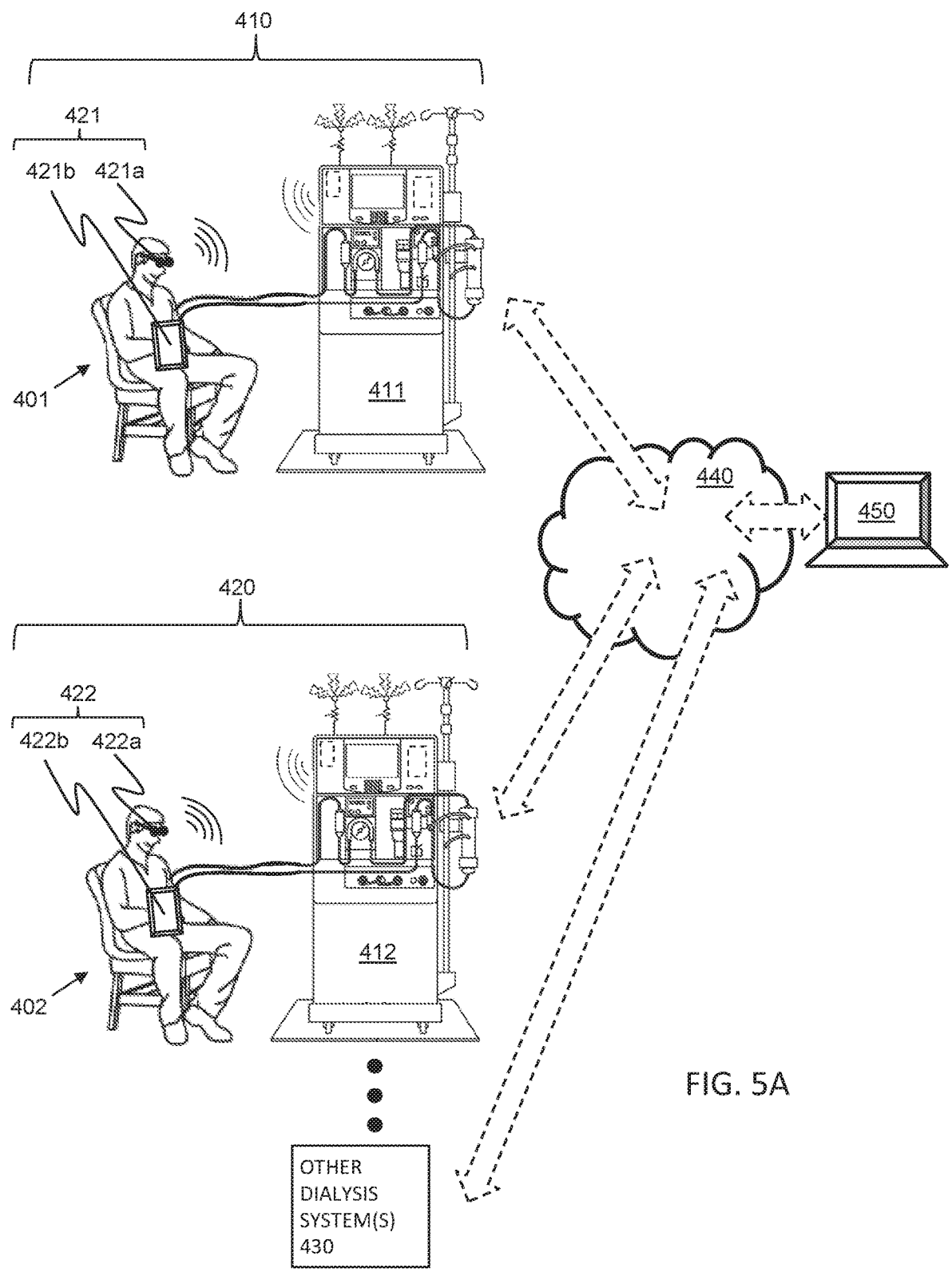
FIGS. 5A and 5B are schematic illustrations showing a system of two (or more) remotely located dialysis machines that are performing dialysis treatments and are scheduling/accessing information via wireless coupling to a remote computer to link dialysis patients together in real-time in a virtual clinic community environment.
Figure 5B:
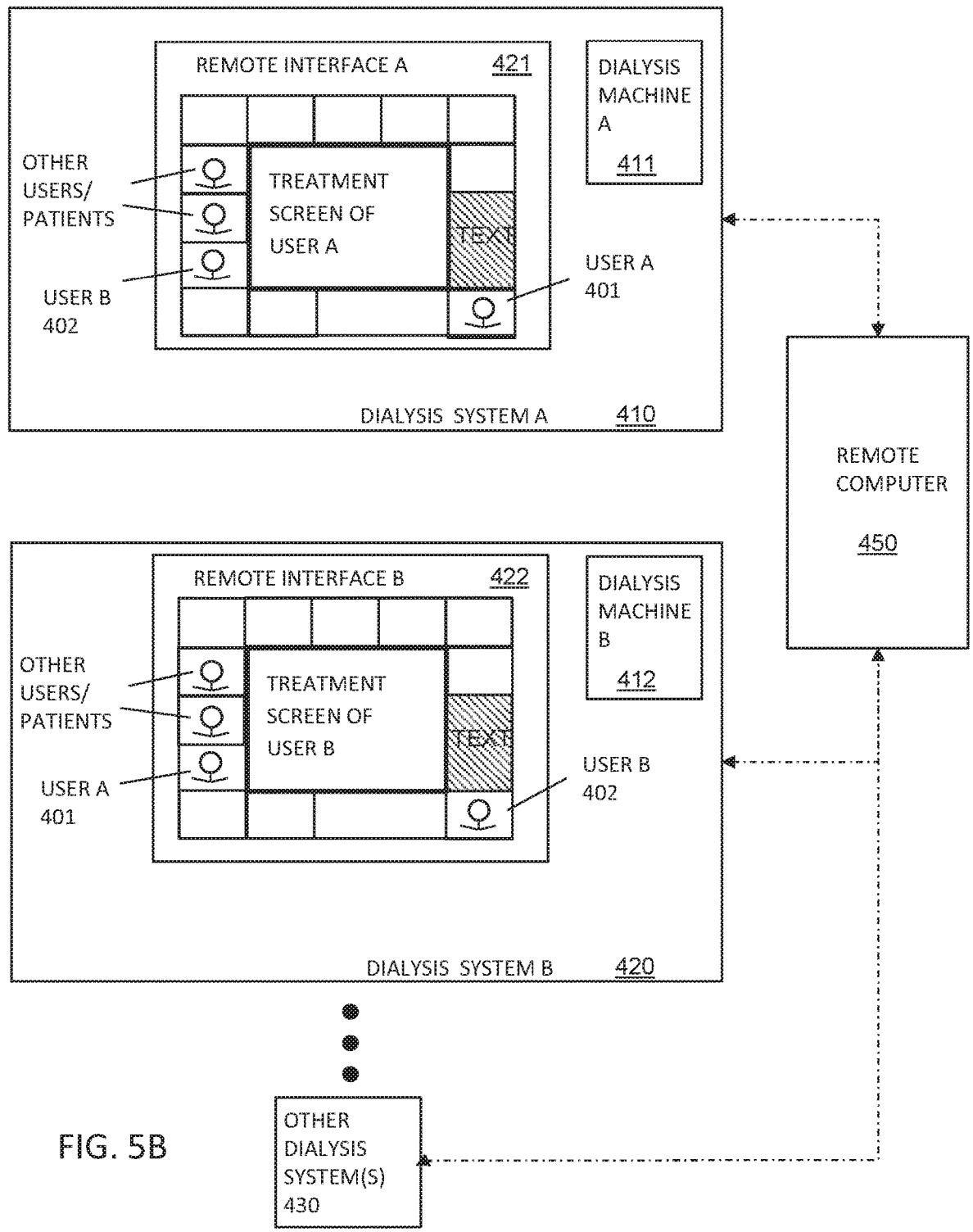

FIGS. 5A and 5B are schematic illustrations showing a virtual dialysis clinic system 400 of two or more remotely located dialysis systems that are performing dialysis treatments. The virtual dialysis clinic system 400 is principally discussed in connection with two dialysis systems 410, 420 but may also be expanded to one or more other dialysis systems 430. The virtual dialysis clinic system 400 provides for accessing information for each of the dialysis systems 410, 420 by a coupling via a network 440 to a remote computer 450 (e.g. processing device having one or more processors, a server and/or database) to link dialysis patients 401, 402 together in real-time in a virtual clinic community environment. The remote computer 450 may store information obtained from the dialysis systems 410, 420 in connection with scheduling of the participants for the social virtual dialysis clinic. Specifically, the accessed information may be accessed and used by the remote computer in scheduling one or more virtual dialysis clinics among participants sharing a commonality of at least one treatment characteristic or parameter, such as treatment type, treatment length, treatment frequencies, time of day of treatment, and/or other treatment characteristics that would be suitable as a basis for scheduling the members of the social virtual dialysis clinic. For example, the scheduling of the participants may be based on patients undergoing dialysis at the same time (i.e. time of day) for a similar length of time.

The remote computer 450 may perform the processing to schedule and/or host one or more instances of the social virtual dialysis clinic among participants and may use social platform interaction functionality. The remote computer 450 may establish communication links over a network with each of the dialysis systems 410, 420 to provide the social interaction functionality that may include streaming of real-time social interactions among the participants of the social virtual dialysis clinic. In various embodiments, the coupling between the dialysis systems 410, 420 and the remote computer 450 may be via a wired and/or a wireless connection and may involve telecommunication network transmissions, including transmissions via the Internet and/or short-range wireless communication networks, in appropriate circumstances.

As shown in FIG. 5A, the system described herein enables using dialysis treatment information (e.g. treatment types, lengths, frequencies, time(s) of day of treatments), stored by and/or sent by the dialysis systems 410, 420 via the network 440 to the remote computer 450, in connection with scheduling or coordinating of the members of the social virtual clinic community. In the illustrated example, remotely located users, user A 401 and user B 402, are underdoing dialysis treatments via dialysis machines 411, 412, respectively. The users 401, 402 may engage in the social virtual dialysis clinic environment via remote interfaces 421, 422. In various implementations, the remote interfaces 421, 422 may be interactive interface devices implemented as wearable interface devices 421a, 422a, and/or, in other embodiments, the remote interfaces may be implemented as portable computing devices, such as tablets, smartphones and/or laptop computers 421b, 422b, and be implementations of the devices 225/226 discussed in connection with FIG. 2. It is further noted that in yet other embodiments according to the system described herein, rather than using remote interfaces, one or more users may engage in the social virtual dialysis clinic environment using integrated displays incorporated directly into the dialysis machines like that of the system discussed in connection with FIG. 1.

FIG. 5B schematically illustrates information displayed for the users A 401, B 402 of the dialysis systems—labeled dialysis system A 410 and dialysis system B 420. The information is displayed on respective displays of the remote interfaces A and B of the user A 401 and user B 402. As shown, on the remote interface A 421, displayed for user A 401 is a dialysis treatment screen with treatment information for the dialysis treatment being performed on user A 401 by the dialysis machine A 411 of the dialysis system A 410. Also displayed on the remote interface A 421 of user A 401 is social interaction information of the virtual dialysis clinic according to the system described herein. The social interaction information may include a picture, a representation and/or live video of user A that is displayed on the remote interface A 421. The social interaction information may then further include information of other users, including, for example, social interaction information of user B 402 that enables the user A to engage with user B and/or the other users of the virtual dialysis clinic while both the user A and the user B are undergoing medical treatments with their respective dialysis systems A 410 and B 420.

Similarly, as shown on remote interface B 422, displayed for user B 402 is a dialysis treatment screen with treatment information for the dialysis treatment being performed on user B 402 by the dialysis machine B 412 of the dialysis system B 420. Also displayed on the remote interface B 422 of user B 402 is social interaction information of the virtual dialysis clinic according to the system described herein. The social interaction information may include a picture, a representation and/or live video of user B that is displayed on the remote interface B 422. The social interaction information may then further include information of other users, including, for example, social interaction information of user A 401 that enables the user B to engage with user A and/or the other users of the virtual dialysis clinic while both the user A 401 and the user B 402 are undergoing medical treatments with their respective dialysis systems A 410 and B 420. The social interaction information may further include text based interactions.

In various embodiments, the representations of users on the displays may be real time images based on camera images or video and/or may be displayed representations of users using avatars or other representational pictures. Social interaction of the virtual dialysis clinic using the interfaces discussed herein may be implemented using social media platforms and functionalities, including text, audio/verbal and/or video based messaging or chat room technologies, as well as interactive gaming functionalities and features.

In another embodiment, a method of providing dialysis treatment is provided that includes providing a platform by which to interact virtually with other dialysis patients undergoing treatment at the same time. The method further includes performing a medical treatment on those patients at a location remote from other dialysis patients, but preserving sense of community and support structure, often cited as a benefit of clinic dialysis groups, via the social interaction functionalities of the virtual dialysis clinic environment.

Figure 6:
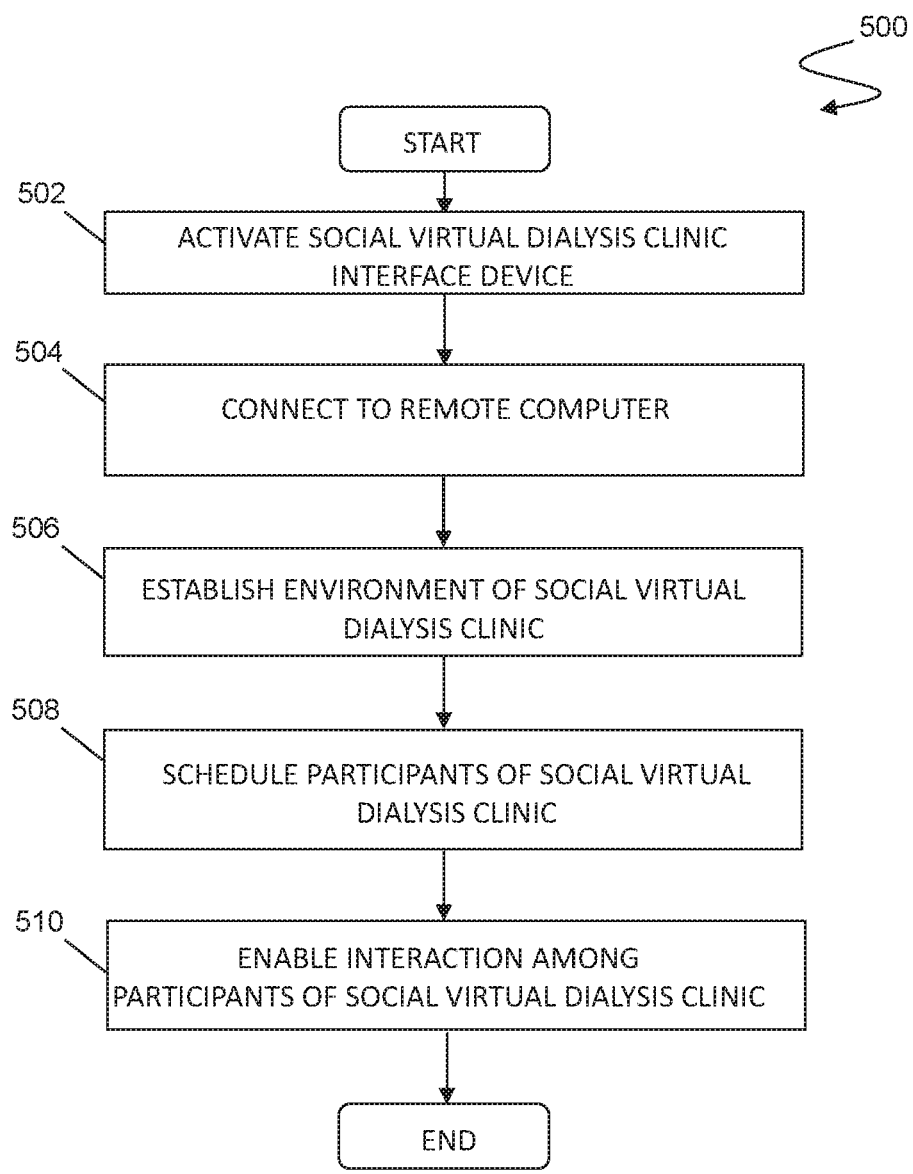
FIG. 6 is a flow diagram detailing processing for a social virtual dialysis clinic according to an embodiment of the system described herein.

FIG. 6 is a flow diagram 500 showing processing for a social virtual dialysis clinic according to an embodiment of the system described herein. At a step 502, an interface device of the social virtual dialysis clinic of the system described herein may be activated, for example, by a user. In various embodiments, the activations process may include logging into the virtual dialysis clinic environment using appropriate security protocols and may include agreement acknowledgment by the user to enter the social virtual dialysis clinic environment. After the step 502, at a step 504 a connection is established from the dialysis system (e.g. dialysis system 100, 200), including social virtual interface device of the system described herein, to a remote computer (e.g. processing device, server and/or database) that facilitates participation and scheduling of the social virtual dialysis clinic. The connection may include one or more wired and/or wireless channels from the dialysis system to the remote computer that enable a data transfer or exchange between the dialysis system and the remote computer.

After the step 504, at a step 506 an instance of the social virtual dialysis clinic environment is established according to the system described herein. The instance may be established according to a social virtual platform technology for enabling a virtual gathering of participants in the virtual environment. Social virtual platform technologies include social media based text platforms, picture/photo exchanging platforms and/or real time audio or video exchanges. Other types of social virtual platform technologies that may be used include gaming and/or chat room based platforms. The social virtual platforms may be public and/or private and utilize scheduling functions according to the system described herein.

After the step 506, at a step 508, participants of a social virtual dialysis clinic may be scheduled according to information exchanged by the dialysis system and the remote computer. As further discussed elsewhere herein, scheduling of the social virtual dialysis clinic may be performed based on specific information corresponding to dialysis treatments of the participants, such as commonalities among participants of treatment types, times, frequencies, and/or durations, among other appropriate treatment characteristics. A centralized remote computer may maintain information on the treatments of multiple users using multiple dialysis systems, and that stored information may be used in the scheduling of the social virtual dialysis clinics among subscribing participants.

After the step 508, at a step 510 scheduled participants of the instance of the social virtual dialysis clinic may interact and/or engage one another using their respective interface devices in order to facilitate a social virtual clinic environment shared by the participants while the participants are undergoing dialysis treatments controlled by their respective dialysis systems. The interaction may include text, picture audio and/or video exchanges among participants and may utilize available social media platforms. The display for the interaction may include one portion for the social interaction and another portion that contains information of the individual user's dialysis treatment thereby providing an integrated social and medical treatment display that may be viewed by the user during the dialysis treatment. After the step 510, processing is concluded for the iteration of the method being described, noting that the interaction enabled by the social virtual dialysis clinic may continue until cessation of the social virtual dialysis clinic and that multiple iterations of the method for the social virtual dialysis clinic may be provided according to the system described herein.

Various embodiments discussed herein may be combined with each other in appropriate combinations in connection with the system described herein. Additionally, in some instances, the order of steps in the flow diagrams, flowcharts and/or described flow processing may be modified, where appropriate. Further, various aspects of the system described herein may be implemented using software, hardware, a combination of software and hardware and/or other computer-implemented modules or devices having the described features and performing the described functions. The system may further include a display and/or other computer components for providing a suitable interface with a user and/or with other computers.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, an SD card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A device for performing medical treatments and simulating social aspects of a medical clinic environment, comprising:
    a medical treatment machine configured to perform a medical treatment on a first patient; and
    an interactive display device configured to interface with a remote computer to exchange information with the remote computer, the interactive display device configured to display, on a single display, a first frame and a plurality of second frames, wherein:
        the first frame includes medical treatment information of the first patient for visual monitoring of the medical treatment that the first patient is undergoing; and
        each of the plurality of second frames includes a respective representation of one of a plurality of other patients and enables the first patient to engage with the one of the plurality of other patients through a remote social interaction while the first patient and the one of the plurality of other patients are undergoing their respective medical treatments,
    wherein the plurality of second frames are positioned outside of the first frame and adjacent to the first frame in the single display, and
    wherein a characteristic of the medical treatment being performed by the medical treatment machine is transmitted to the remote computer and is used in scheduling the first patient and the one of the plurality of other patients for the remote social interaction to be performed while the medical treatment machine performs the medical treatment, wherein the characteristic of the medical treatment includes a treatment frequency of the medical treatment, a treatment length of the medical treatment, or both.

2. The device according to claim 1, wherein the scheduling is performed automatically by the remote computer according to a commonality in the characteristic of the medical treatment among the first patient and the plurality of other patients.

3. The device according to claim 1, wherein the interactive display device wirelessly exchanges information directly with the remote computer.

4. The device according to claim 1, wherein the interactive display device wirelessly exchanges information with the remote computer via an intermediary device.

5. The device according to claim 4, wherein the intermediary device is a transceiver device of the medical treatment machine.

6. The device according to claim 1, wherein the interactive display device is incorporated into the medical treatment machine.

7. The device according to claim 1, wherein the interactive display device is remote from the medical treatment machine.

8. The device according to claim 7, wherein the interactive display device is a portable processing device carried or worn by the first patient that displays information to the first patient and receives input from the first patient.

9. The device according to claim 1, wherein the medical treatment machine is a dialysis machine.

10. The device according to claim 1, wherein the characteristic of the medical treatment includes one or more of a treatment type of the medical treatment, or a time of day of treatment of performing the medical treatment.

11. A social virtual dialysis clinic system, comprising:
    a first medical treatment machine that is configured to perform a first medical treatment on a first user;
    a second medical treatment machine, remote from the first medical treatment machine, that is configured to perform a second medical treatment on a second user;
    a first interactive display device coupled to the first medical treatment machine and configured to interface with a remote computer to exchange information with the remote computer, the first interactive display device configured to display, on a single display, a first frame and a second frame, wherein the second frame is positioned outside of the first frame and adjacent to the first frame and wherein:
        the first frame includes first medical treatment information of the first user for visual monitoring of the first medical treatment that the first user is undergoing, and
        the second frame includes a representation of the second user and enables the first user to engage with the second user through a remote social interaction while the first user is undergoing the first medical treatment and the second user is undergoing the second medical treatment; and
    a second interactive display device coupled to the second medical treatment machine and configured to interface with the remote computer to exchange information with the remote computer, the second interactive display device configured to display, on another single display, a third frame and a fourth frame, wherein the fourth frame is positioned outside of the third frame and adjacent to the third frame and wherein:
        the third frame includes second medical treatment information of the second user for visual monitoring of the second medical treatment that the second user is undergoing, and
        the fourth frame includes a representation of the first user and enables the second user to engage with the first user through the remote social interaction while the second user is undergoing the second medical treatment and the first user is undergoing the first medical treatment, wherein the remote computer uses treatment characteristics of the first and the second medical treatments to schedule the remote social interaction between the first and the second users, a treatment characteristic including at least one of treatment length, a treatment frequency, or a time of day of respective medical treatment.

12. The system according to claim 11, wherein a first characteristic of the first medical treatment being performed by the first medical treatment machine is transmitted to the remote computer, and wherein a second characteristic of the second medical treatment being performed by the second medical treatment machine is transmitted to the remote computer, and wherein the first characteristic and the second characteristic are used in scheduling the first user and the second user for a remote social interaction using the first interactive display device and the second interactive display device while the first medical treatment machine and the second medical treatment machine perform the first medical treatment and the second medical treatment, respectively.

13. The system according to claim 11, wherein at least one of the first interactive display device or the second interactive display device wirelessly exchanges information directly with the remote computer.

14. The system according to claim 11, wherein at least one of the first interactive display device or the second interactive display device wirelessly exchanges information with the remote computer via an intermediary device.

15. The system according to claim 14, wherein the intermediary device includes a transceiver device of at least one of the medical treatment machines.

16. The system according to claim 11, wherein at least one of the first interactive display device and the second interactive display device is incorporated into a corresponding one of the first medical treatment machine or the second medical treatment machine.

17. The system according to claim 11, wherein at least one of the first interactive display device or the second interactive display device is remote from a corresponding one of at least one of the first medical treatment machine and the second medical treatment machine.

18. The system according to claim 17, wherein at least one of the first interactive display device or the second interactive display device is a portable processing device carried or worn by a user that displays information to the user and receives input from the user.

19. The system according to claim 11, wherein at least one of the first medical treatment machine or the second medical treatment machine is a dialysis machine configured to be used remote from a medical clinic.

20. The system according to claim 11, wherein the first medical treatment machine has a type that is different from the second medical treatment machine, the type being selected from a group of systems consisting of: a hemodialysis system, a peritoneal dialysis system, and a chemotherapy treatment system.

* * * * *